United States Patent
Hung et al.

(10) Patent No.: US 9,505,687 B2
(45) Date of Patent: Nov. 29, 2016

(54) SYNTHESIS OF DIIODOPERFLUORO-$C_3$ TO $C_7$-ALKANES

(71) Applicant: THE CHEMOURS COMPANY FC, LLC, Wilmington (DE)

(72) Inventors: Ming Hong Hung, Wilmington (DE); Alexander Anthony Marchione, Haddon Heights, NJ (US); Peter A. Morken, Wilmington (DE)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 15/053,634

(22) Filed: Feb. 25, 2016

(65) Prior Publication Data

US 2016/0251285 A1     Sep. 1, 2016

Related U.S. Application Data

(60) Provisional application No. 62/126,303, filed on Feb. 27, 2015.

(51) Int. Cl.
*C07C 17/395* (2006.01)
*C07C 17/26* (2006.01)
*C07C 17/263* (2006.01)
*C07C 17/013* (2006.01)
*C07C 17/093* (2006.01)

(52) U.S. Cl.
CPC ........... *C07C 17/395* (2013.01); *C07C 17/013* (2013.01); *C07C 17/093* (2013.01); *C07C 17/26* (2013.01); *C07C 17/263* (2013.01)

(58) Field of Classification Search
CPC .... C07C 17/26; C07C 17/263; C07C 17/395
See application file for complete search history.

(56) References Cited

U.S. PATENT DOCUMENTS

| | | | |
|---|---|---|---|
| 4,948,852 A | 8/1990 | Moore | |
| 5,231,154 A | 7/1993 | Hung | |
| 6,002,055 A | 12/1999 | Yang | |
| 6,277,937 B1 | 8/2001 | Duvalsaint et al. | |
| 6,825,389 B2 | 11/2004 | Dindi et al. | |

FOREIGN PATENT DOCUMENTS

| | | |
|---|---|---|
| WO | 2014/062450 A2 | 4/2014 |
| WO | 2014/062469 A1 | 4/2014 |

OTHER PUBLICATIONS

Yang, Z-Y. "Environmentally Benign Processes for Making Useful Fluorocarbons: Nickel-or Copper(I) Iodide-Catalyzed Reaction of Highly Fluorinated Epoxides with Halogens in the Absence of Solvent and Thermal Addition of CF2I2 to Olefins" J. Org. Chem. 2004, 69, pp. 2394-2403.*

Yang, Zhen-Yu, Nickel-Catalyzed Reaction of Highly Fluorinated Epoxides with Halogens, Journal of American Chemical Society, 1996, pp. 8140-8141, vol. 118.

Yang, Zhen-Yu, Preparation of Highly Fluorinated Cyclopropanes and Ring-Opening Reactions with Halogens, Journal of Organic Chemistry, 2003, pp. 4410-4416, vol. 68.

* cited by examiner

*Primary Examiner* — Jafar Parsa
*Assistant Examiner* — Medhanit Bahta

(57) ABSTRACT

The present invention is the process comprising forming a stable mixture comprising $I(CF_2)_nI$, wherein n is at least 3 and at least one of $I(CF_2)_nI$, wherein n is 1 or 2, as a contaminant in said mixture and heating said mixture to a temperature of at least 220° C. to reduce the amount of said contaminant to be no greater than 1% when said contaminant is $ICF_2I$ (n=1) and no greater than 0.1% when said contaminant is $ICF_2CF_2I$ (n=2).

10 Claims, No Drawings

SYNTHESIS OF DIIODOPERFLUORO-C$_3$ TO C$_7$-ALKANES

BACKGROUND INFORMATION

1. Field of the Disclosure

This invention relates to the synthesis of diiodoperfluoro-C$_3$ to C$_7$-alkanes I(CF$_2$)$_n$I, wherein n is 3 to 7 that produces little to no diiodoperfluoromethane (ICF$_2$I) and diiodoperfluoroethane (I(CF$_2$)$_2$I).

2. Description of the Related Art

U.S. Pat. No. 6,002,055 discloses that dihaloperfluoroalkanes are useful as chain transfer agents for fluoroelastomers. This patent also discloses the synthesis of dihalodifluoromethanes and their homologues by reacting a fluorinated epoxide with dihalogen in the presence of catalyst, also referred to as metal promoter. Hexafluoropropylene oxide (HFPO) is the preferred epoxide and iodine appears to be the preferred halogen. Fifteen of the twenty-one Examples use iodine as the halogen. The catalyst is a zero-valent metal, examples of which are Ni and Cu or combinations of metals such as Ni/Cu, Ni/Zn, or a metal halide such as CuI. The catalyst is usually in the form of a metal slurry or may be the Ni alloy, such as Hastelloy® C, that lines the process vessel. The importance of the catalyst is expressed in terms of low yield when the catalyst is not present during the reaction, resulting in the yield of dihalodifluoromethanes and homologs, not being greater than about 30%. When excess HFPO is used as the reactant, it is disclosed that the major product is the higher homologues such as I(CF$_2$)$_3$I, diiodoperfluoropropane, as shown in Example 2. Example 2 discloses the reaction between 254 g of iodine with 500 g of HFPO, mol ratio (HFPO/iodine of 3.1 to 1, carried out in a Hastelloy® C autoclave at a temperature of 185° C. for 30 hours. In addition to substantial formation of CF$_3$COF (perfluoroacetyl fluoride) (PAF) gas, the diiodoperfluoroalkane formation in the reaction product is as follows:

| Diiodoperfluoroalkane | GC area % |
|---|---|
| ICF$_2$I | 7.1 |
| ICF$_2$CF$_2$I | 1 |
| ICF$_2$CF$_2$CF$_2$I | 58.7 |
| I(CF$_2$)$_4$I | 0.86 |
| I(CF$_2$)$_5$I | 0.33 |

A principal disadvantage of this result is the formation of relatively large amounts of ICF$_2$I and ICF$_2$CF$_2$I accompanying the formation of the higher homologues. The compound ICF$_2$CF$_2$I is a chain termination agent when present in the polymerization process to make fluoroelastomers, and must be removed from the reaction product before the reaction product is used in the polymerization to make fluoroelastomer.

WO 2014/062450 discloses a process for making diiodoperfluoroalkanes of the formula I(CF$_2$)$_n$I where n=3 to 11, and where the amount of compounds of the formula I(CF$_2$)$_n$I, where n is 1 or 2, is small. The n=1 and n=2 compounds are disclosed to be toxic or hazardous. In addition, it is difficult to remove these compounds from the reaction product containing the higher homologues. '450 teaches the making of the diiodoperfluoroalkanes by reacting HFPO with iodine in the presence of a combination of metal catalysts, as follows: at least one of (a) a first metallic compound and a second metallic compound comprising molybdenum or (b) a metallic alloy that contains certain amounts of Ni and Mo. The first metallic compound preferably has a high surface area such as provided by a finely divided powder, but can be present as the liner of the reactor within which the reaction is carried out. Alternatively, the second metallic compound can be the metal lining of the reactor. Another alternative embodied in Examples 4-9 is the metal alloy being the reactor lining along with perforated Ni ribbon positioned within the reactor. The use of a molar ratio of HFPO to iodine of at least 3.2, at least 3.6, or even at least 3.9 is disclosed to provide selectivity in the reaction process to drive the reaction more towards the formation of the n=3 to 11 diiodoperfluoroalkanes, minimizing the formation of the n=1 and 2 compounds. The selection of the first and second metals or the metal alloy also contributes to this selectivity. The Examples, in which the reaction temperature is 170° C., disclose that when only Ni catalyst is present by addition to the reaction (Comparative Examples A and B), the amount of ICF$_2$I and ICF$_2$CF$_2$I formed are relatively large as reported in Table 1. Tables 3 and 6 report the formation of smaller amounts of these compounds when a combination of metal catalyst is used. These tables also report the formation of large molecule compounds, e.g. I(CF$_2$)$_8$I, ICF$_2$CF$_2$CF(CF$_3$)C(=O)F, and CF$_3$CF(I)CF$_2$CF$_2$I. These compounds as well as the CF$_3$CF(I)C(=O)F and CF$_3$I are deleterious to the polymerization process to make fluoroelastomer and therefore require a removal step before the reaction product can be used in polymerization to make fluoroelastomer. The presence of the catalyst, at least one of which is not the reactor lining also requires a removal step, all of which adds to the cost of the catalytic process of '450.

SUMMARY

The present invention has discovered that I(CF$_2$)$_n$I, wherein n is 3 to 7, can be made in high yield by reacting HFPO with iodine, without the formation of any significant amount of I(CF$_2$)$_n$I, wherein n is 1 or 2, as a contaminant and preferably without the need for any added catalyst to obtain this result. This saves the need for removing catalyst and contaminant from the I(CF$_2$)$_{3-7}$I reaction product This also saves the need removing other contaminants such as higher homologues of I(CF$_2$)$_n$I, wherein n is at least 8. The reaction product containing the I(CF$_2$)$_n$I, wherein n is 3 to 7 can be used as is in the polymerization processes as a telogen such as to make fluoroelastomer incorporating iodine as a cure site.

This discovery is embodied in the process comprising forming a stable mixture comprising I(CF$_2$)$_n$I, wherein n is at least 3 and at least one of I(CF$_2$)$_n$I, wherein n is 1 or 2, as a contaminant in said mixture and heating said mixture to a temperature of at least 220° C. to reduce the amount of said contaminant to be no greater than 1% when said contaminant is ICF$_2$I (n=1) and no greater than 0.1% when said contaminant is ICF$_2$CF$_2$I (n=2). The wording "no greater than" the indicated amounts of the two contaminants is intended to include no measurable amounts of either or both contaminants. The reduction in the amount of one or both of these contaminants when present is preferably at least 50% compared to a process carried out without heating the stable mixture to a temperature of at least 220° C.

The characterization of the mixture being stable prior to heating to a temperature of at least 220° C. is in contrast to the mixture being transitory during this heating, in terms of what happens to the ICF$_2$I and ICF$_2$CF$_2$I contaminant compounds in the stable mixture. The ICF$_2$I and/or ICF$_2$CF$_2$I compounds are typically present in the mixture prior to heating, and the heating decomposes them, whereby they are no longer present in more than the small amounts indicated above and one or both compounds are preferably not present at all in measurable amounts. Without this heating, the contaminant compounds remain present in the mixture in greater amounts than the respective amounts stated above. Thus, the process of the present invention is a multi-step thermal process for eliminating the presence of most if not all of the undesired $ICF_2I$ and $ICF_2CF_2I$ compounds in the stable mixture.

The time of heating to a temperature of 220° C. or higher is effective to eliminate the presence of most if not all of the undesired $ICF_2I$ and $I(CF_2)_2I$ compounds to obtain not more than the small amounts indicated above for these compounds. The $I(CF_2)_nI$ compounds, wherein n is at least 3, remaining in the mixture, are thermally stable at the temperature of heating to at least 220° C. This heating temperature and time of heating should be less than that which causes decomposition of the $I(CF_2)_nI$ compounds, wherein n is at least 3 or n is 3 to 7.

The % amounts of $I(CF_2)_nI$, compounds wherein n is 1 or 2 ($ICF_2I$ and $ICF_2CF_2I$) refers to the peak area corresponding to the particular compound compared to all other peak areas under the curve obtained by gas chromatograph analysis (GC) of the reaction product being analyzed, which is preferably after the heating step. The same is true for % amounts with reference to other $I(CF_2)_nI$ compounds disclosed herein. Thus, the % amount may also be referred to as the GC area % or simply area %. The GC area % is an approximation of mol %.

The thermal process of the present invention is characterized by the following preferences, individually or collectively in whole or part:
1. The stable mixture is the reaction product of a chemical reaction in a reactor. It is this reaction product that contains at least one of the $I(CF_2)_nI$, compounds wherein n is 1 or 2. According to this preference, the thermal process is a multi-step process comprising first the conduct of the chemical reaction, e.g. at a temperature less than 220° C., and then the heating of the reaction product to a temperature of at least 220° C.
2. The reaction product obtained from the chemical reaction is the direct reaction product, which is then subjected to washing as described under the Examples to form the purified reaction product. These reaction products are defined under the Examples. The GC analysis results reported herein are obtained from the purified reaction product.
3. The chemical reaction is conducted without the need for catalyst being present, i.e. in contact with the chemical reaction, in order to obtain the reaction product in which the presence of the $ICF_2I$ and $I(CF_2)_2I$, compounds in the reaction mixture is no greater than the amounts indicated above after being subjected to the heating to at least 220° C.
4. Preferably, the chemical reaction is carried out in the absence of added catalyst. The absence of added catalyst means to the absence of catalyst added within or into the chemical reaction carried out in the reactor. The interior surface such as a lining of the reactor, if the interior surface were a catalyst, is not an added catalyst, because the interior surface borders the chemical reaction and therefore is not within the chemical reaction. The chemical reaction, such as between hexafluoropropylene oxide and iodine to be described hereinafter, achieves the goals upon heating to a temperature of at least 220° C., of the contaminants $ICF_2I$, and $ICF_2CF_2I$, when one or both are present, being present in amounts of no greater than 1% and 0.1%, respectively, in the purified reaction product.
5. The reactor may have a metal lining which has the primary function of resistance to corrosion by the chemical reaction or the thermal process, but which also might exhibit some catalytic activity that is superfluous to achieving the high selectivity to obtaining the compounds $I(CF_2)_nI$ wherein n is 3 to 7 achieved by the multi-step thermal process of the present invention. The purified reaction product mentioned above, contains $I(CF_2)_3I$ as the predominant component. Preferably, this reaction product contains at least 70% (GC area) of the $I(CF_2)_3I$ compound as the predominant component. Reference to the $I(CF_2)_3I$ compound as the predominant component means that perfluoroacetyl fluoride by-product of the chemical reaction and gases associated are already removed from the reaction product, leaving the mixture of compounds $I(CF_2)_nI$, wherein n is at least 1, such as 1 to 7, comprising the reaction product. The PAF and associated gases and traces of iodine are removed from the reaction product prior to determining the amount of one or more compounds of the homologous series $I(CF_2)_nI$, wherein n is at least 1, in the reaction product by GC analysis. Preferably, in all embodiments of the present invention disclosed herein, the gases removed from the reaction product prior to GC analysis have a boiling point of 0° or less. PAF boils at −59° C.

According to one embodiment of the multi-step thermal process of the present invention, this process is carried out first to obtain the reaction product of the chemical reaction between iodine and hexafluoropropylene oxide (HFPO) at a temperature less than 220° C. This chemical reaction is one step of the multi-step process and the heating to a temperature of at least 220° C. is another (second) step in this process. The chemical reaction and heating to at least 220° C. are not simultaneous steps. The above-described preferences apply to each embodiment of the multi-step process involving the reaction between iodine and HFPO described hereinafter.

The reaction product of the HFPO/iodine chemical reaction that is heated to at least 220° C. can be the entire reaction product or a portion of the entire reaction product. For example, perfluoroacetyl fluoride (PAF) is a by-product of the HFPO/iodine chemical reaction. Some or all of this PAF can be removed from the entire reaction product before exposure to heating step (at least 220° C.) of the thermal process.

This multi-step thermal process wherein HFPO is reacted with iodine is preferably carried out in the absence of added catalyst. This process is also preferably carried out to obtain $I(CF_2)_3I$ as the predominant component of the reaction product as described above.

The multi-step thermal process of the present invention is also characterized by the following preferences, individually or collectively in whole or part:
1. The $I(CF_2)_nI$ compounds, wherein n is at least 3, in the purified reaction product contain the homologue mixture of $I(CF_2)_nI$ wherein n is 3 to 7. Preferably, the compound $I(CF_2)_3I$, in this homologue mixture comprises at least 70% of the homologue mixture. This high proportion of the formation of $I(CF_2)_3I$ in the chemical reaction leads to little to no formation of $I(CF_2)_nI$ compounds wherein n is at least 8.
2. The yield of the reaction product (purified) in the chemical reaction between HFPO and iodine is at least 70%. Yield % is defined under the Examples.

3. The chemical reaction between the iodine and the HFPO is carried out at a temperature of less than 220° C. and more preferably at a temperature of 150° C. to 210° C. prior to heating the stable mixture/reaction product to a temperature of at least 220° C. Exposure of this stable mixture/reaction product to this higher heating is carried out to be effective to eliminate the presence of most if not all of the undesired $ICF_2I$ and $I(CF_2)_2I$ compounds to obtain not more than the small amounts indicated above for these compounds, without causing decomposition of higher members of the homologous series $I(CF_2)_nI$, wherein n is at least 3, preferably 3 to 7.

4. The molar proportion of HFPO to iodine in the chemical reaction is at least 3.3.

The multi-step thermal process of the present invention includes the chemical reaction between iodine and hexafluoropropylene oxide (HFPO) carried out stepwise in a vent-charge process in a reactor. This vent-charge thermal process comprises the steps of (a) reacting the iodine with a portion of the total amount of the hexafluoropropylene oxide to be reacted with the iodine, at the temperature of 150° C. to 210° C., thereby forming the reaction product containing gaseous perfluoroacetyl fluoride as a reaction by-product, (b) cooling the reaction product to become liquid except for gaseous perfluoroacetyl fluoride, (c) venting the perfluoroacetyl fluoride from said reactor, and (d) repeating the steps (a), (b), and (c) until the remainder of the total amount of the hexafluoropropylene oxide is reacted with the iodine, and (e) heating the reaction product to at least 220° C. being carried at least after the last step (a) of the repeating said steps (a), (b) and (c), to obtain as a result thereof, said reaction product comprising the homologue mixture of compounds $I(CF_2)_nI$, wherein n is 3 to 7 contaminated with at least one of $ICF_2I$ and $I(CF_2)_2I$, wherein as a result of said heating of step (e), no greater than 1% of said $ICF_2I$ and no greater than 0.1% of said $I(CF_2)_2I$ are present in said reaction product.

In this embodiment, the heating step can be carried out on the entire reaction product, prior to venting, i.e. the heating step is practiced after each step (a), i.e. prior to any steps (b) and (c). Alternatively, the heating step can be carried out only on the reaction product free of PAF, i.e. after the venting step(s) (c).

The venting steps (c) impart the advantage to the vent-charge embodiment of permitting the chemical reaction to be carried out at a lower pressure within the reactor than if the venting were postponed until completion of the reaction. This pressure lowering is considerable, since one mole of PAF is formed from each mole of HFPO consumed in the reaction. A lower pressure-operated reactor, including associated equipment including seals, is less expensive than a higher pressure-operated reactor.

This vent-charge process embodiment includes the foregoing described preferences and also the following preferences, individually or collectively, in whole or in part:

1. The heating of the reaction product to at least 220° C. is carried out after each step (a) of the repeating of said steps (a), (b), and (c).

2. The reaction product after the last step (a) comprises the $I(CF_2)nI$, wherein n is at least 3, said $I(CF_2)nI$, wherein n is at least 3, being the homologue mixture of $I(CF_2)nI$ wherein n is 3 to 7.

3. The compound $I(CF_2)_3I$, comprises at least 70% of the homologue mixture of the compounds $I(CF_2)nI$, wherein n is at least 3, and of the homologue mixture of $I(CF_2)nI$ wherein n is 3 to 7.

4. The molar proportion of the total amount of the hexafluoropropylene oxide reacted with the iodine in said chemical reaction is at least 3.0, more preferably 3.3.

5. The portion of the hexafluoropropylene oxide reacted with the iodine in each of step (a) is from 10 to 50% of the total amount of the hexafluoropropylene oxide reacted with the iodine.

DETAILED DESCRIPTION

The multi-step thermal process of the present invention is preferably carried out in a reactor under the autogenous pressure of the chemical reaction in the first thermal step of the process. In the chemical reaction between iodine and HFPO, both gaseous at the temperature of the chemical reaction, the increase in pressure within the reactor arises primarily from the formation of PAF gaseous by-product. The increase in autogenous pressure accompanying the formation of the PAF can result in liquid phase coexisting with gases within the reactor during the chemical reaction, depending on the temperature and pressure within the reactor. In the vent-charge embodiment, the pressure within the reactor is relieved by the periodic venting of the PAF from the reactor as described above. The reactor or its lining may be constructed from material that can be catalytic to the chemical reaction or non-catalytic. Any catalytic effect of the material of construction of the reactor is moderated by the fact that the material of construction merely forms the boundary for the reaction and is not within the reaction, as catalyst in some discrete or particulate form, such as wire, ribbon or particles. This moderating effect is demonstrated by Comparison Example A wherein after the reaction of HFPO with iodine at 190° C., there is no heat-up step to at least 220° C. The result is a purified reaction product containing excessive amounts of $ICF_2I$ and $I(CF_2)_2I$ even though the reactor in which the HFPO/iodine reaction is carried out is made of Hastelloy® C, which is disclosed in U.S. Pat. No. 6,002,055 as being a catalyst. Examples 15-17 disclose the beneficial effect of heating the reaction product to 230° C. in providing greatly reduced amounts of $ICF_2I$ and $I(CF_2)_2I$ in the purified reaction product.

The temperature to which the content of the reactor is heated in the first step for carrying out the chemical reaction, such as between iodine and HFPO, is preferably from 170° C. to 200° C., this lower temperature minimizing unwanted side reactions. The temperature at which the second step of the multi-step thermal process is carried out is preferably from 220° C. to 240° C., more preferably from 225° C. to 240° C. Preferably the heating in the second step reduces the amount of $ICF_2I$ and $I(CF_2)_2I$ by at least to ⅓, more preferably by at least to ⅕, and even more preferably by at least to 1/10, based on comparison of the amounts present in the purified reaction product before and after practice of the second step. These preferences also apply to steps (a) and (d) of the vent-charge embodiment and the results of the practice of the vent-charge embodiment. In this embodiment, the second heating step can be carried out as part of each step (a), i.e. after the reaction is carried out at a temperature in the range of 150° C. to 210° C., preferably 170° C. to 200° C., the resulting reaction product is heated to the higher temperature of at least 220° C. of the second step of the multi-step thermal process. Alternatively, the second heating step can be carried out only one time as part of the last step (a), i.e. on the reaction product after the reaction of all the steps (a) have been conducted.

The molar ratio of HFPO to iodine in the chemical reaction is preferably at least 3.0, more preferably at least 3.4, and more preferably at least 3.5. Preferably, the molar ratio of HFPO to iodine is no greater than 3.8. These preferences apply to the vent-charge embodiment as well.

The reaction is preferably carried out to 100% conversion of the HFPO reactant, whereby there is no need to recover unreacted HFPO.

In the repetition of step (a) of the vent-charge embodiment, it is preferred that only a portion of the total amount of HFPO to be reacted is present in the practice of the first step (a), and additional portions of the HFPO are added in each repetition of step (a) to reach the remainder of the total amount of HFPO to be reacted. Thus, the subsequent reacting steps (s) include the addition (charging) of portions of HFPO to be consumed in the reaction with iodine. Since this charging of the reactor follows the venting of the preceding step (c), the embodiment is referred to as the vent-charge embodiment.

The cooling steps (b) are conveniently carried out by cooling of the reactor content to 0° C. At this temperature, the PAF in the reaction product remains gaseous, while the $I(CF_2)_n I$ homologue mixture, wherein n is 1 to 7, is in the liquid state, enabling the PAF to be separated from the reaction product by venting from the reactor. No HFPO, boiling temperature −27.4° C., is vented with the PAF, because the HFPO has preferably been reacted with the iodine in the reactor.

In the vent-charge embodiment, the total amount of HFPO reacted with the iodine is at least 3.0, more preferably at least 3.3, at least 3.4 or at least 3.5 molar ratio of HFPO to iodine. Preferably, the molar ratio of HFPO to iodine is no greater than 3.8 in the multi-step thermal process, including the vent-charge embodiment.

More preferably, the portion of HFPO added to and present in the reactor for reaction with the iodine in each step (a) of the vent-charge embodiment is 20 to 50% of the total amount of HFPO reacted with the iodine, even more preferably 33 to 50%. Preferably the portion of HFPO reacted in each step (a) is in the same amount.

In the vent-charge embodiment, preferably the total amount of iodine to be reacted is added to the reactor so as to be present in the first step (a).

The time of the exposure of the contents of the reactor to these temperatures is effective to provide result of no more than the small amounts of $ICF_2I$ and $I(CF_2)_2I$ mentioned above. In the multi-step thermal process, the chemical reaction at the lower temperature and then heating to the higher temperature can take at least 2 hours for each step. In the vent-charge embodiment, the times can be less for each step (a) and heating to the higher temperature as part of each step (a). If the heating to higher temperature is delayed until the last step (a), the heating to the higher temperature can also take at least 2 hours.

Preferably the multi-step thermal reaction of HFPO with iodine, including the vent-charge embodiment, produces a reaction product (purified) at a yield of at least 70%, more preferably at least 80%, even more preferably at least 85%, and most preferably at least 90%. For each of these yields of purified reaction product, most of the purified reaction product is a mixture of the homologous series of compounds $I(CF_2)_n I$, wherein n is 1 to 7, and especially wherein n is 3 to 7. In this regard, the purified reaction product produced by the process of the present invention is highly selective in providing these compounds (mixtures), especially wherein n is 3 to 7. For example, when the n is 1 to 7 and 3 to 7, mixtures of these homologous series of compounds comprises preferably at least 90% (GC area), and more preferably at least 92% (GC area) of the purified reaction product. The Examples herein disclose the attainment of even greater amounts of these mixtures of the homologous series of compounds. High purity $I(CF_2)_3I$ can be obtained through distillation from the homologous series of compounds wherein n is 3 to 7. $I(CF_2)_3I$ has a boiling point at 87° C./200 mmHg.

With respect to the series of homologous series of compounds, wherein n is 1 to 7 or 3 to 7, the $I(CF_2)_3I$ preferably comprises at least 70% (GC area), more preferably at least 80% (GC area), and even more preferably at least 85% (GC area), and most preferably at least 90% (GC area) of the purified reaction product. These amounts of $I(CF_2)_3I$ also apply to the comparison of the CG areas of $I(CF_2)_3I$ with the GC areas of the homologous series wherein n is 1 to 7 and wherein n is 3 to 7. These compositions apply to all of the multi-step thermal reactions of HFPO with iodine, including the vent-charge embodiment.

For all these compositions of the purified reaction product, the amounts of $ICF_2I$ and $I(CF_2)_2I$ present in this reaction product are no greater than 1% and 0.1% (GC area), respectively.

The above-mentioned compositions of the purified reaction product also apply to the first mentioned process of the present invention, as the preferred composition of the mixture after the heating step.

A preferred process included in the multi-step process of the present invention is the vent-charge embodiment involving the chemical reaction between iodine and hexafluoropropylene oxide in a reactor to form a reaction product comprising the homologue mixture of $I(CF_2)_n I$, wherein n is 3 to 7, which contains at least one of the contaminants $ICF_2I$ and $I(CF_2)_2I$. This process comprises the steps of:

(a) reacting iodine with HFPO at a temperature of 150° C. to 210° C. in a reactor, the amount of said HFPO being a portion of the total amount of HFPO to be reacted with said iodine, thereby forming a reaction product containing gaseous perfluoroacetyl fluoride as a reaction by-product, (b) cooling said reaction product to become liquid except for said gaseous perfluoroacetyl fluoride, (c) venting said perfluoroacetyl fluoride from said reactor, (d) repeating said steps (a), (b), and (c) until said total amount of said HFPO is reacted with said iodine, and (e) heating said reaction product to at least 220° C. at least after the last step (a) of said repeating said steps (a), (b) and (c), to obtain as a result thereof a mixture of compounds comprising $I(CF_2)_n I$, wherein n is 3 to 7 and wherein presence of the compound when n is 1 ii said mixture is no greater than 1% and the presence of the compound when n is 2 in said mixture is no greater than 0.1%.

Each repetition of step (a) preferably includes charging an additional portion of said HFPO to said reactor, such that the total amount of HFPO charged to the reactor in all the steps (a) is one of the minimum molar ratios mentioned above. The details and preferences mentioned above with respect to the multi-step thermal process and the vent-charge embodiment are applicable to this preferred process.

Another preferred process of the present invention comprises reacting HFPO with iodine at a temperature of 150° C. to 210° C. to form reaction product comprising the homologue mixture of $I(CF_2)_n I$, wherein n is 3 to 7, which contains at least one of the contaminants $ICF_2I$ and $I(CF_2)_2I$, and thereafter heating the resultant reaction product to a temperature of at least 220° C., to obtain as a result thereof a reaction product comprising said homologue mixture and containing no greater than 1% of $ICF_2I$ and no greater than 0.1% of $I(CF_2)_2I$. The compound $I(CF_2)_2I$ is the predominant component of the reaction product and the compounds $I(CF_2)_nI$, wherein n is 3 to 7 comprise at least 70% of the reaction product. The details and preferences mentioned above with respect to the multi-step thermal process and the vent-charge embodiment are applicable to this preferred process.

EXAMPLES

In the Examples, the diiodoperfluoroalkanes may be referred to as follows:

| | |
|---|---|
| PDA-1 = $ICF_2I$ | PDA-5 = $I(CF_2)_5I$ |
| PDA-2 = $I(CF_2)_2I$ | PDA-6 = $I(CF_2)_6I$ |
| PDA-3 = $I(CF_2)_3I$ | PDA-7 = $I(CF_2)_7I$ |
| PDA-4 = $I(CF_2)_4I$ | |

The gas chromatography GC analysis results, whether disclosed as %, GC area %, or as area % with respect to one or more compounds $I(CF_2)_nI$, wherein n is 1 to 7, are obtained using an Agilent 7890 gas chromatography (GC) system (Santa Clara, Calif.), using a 20% OV-210 packed column (Supelco, Bellefonte, Pa.), with a straight isothermal 160° C. temperature condition, along with a thermal conductivity (TCD) detector. The GC area % of the homologue mixture of the above compounds is the selectivity of the formation of the compound(s) referred to, e.g. the mixture wherein n is 3 to 7 or n is 3 by itself.

All of the reactors referred to in the Examples are made of Hastelloy® C, a metal alloy containing in wt % 56% Ni, 3.5% W, 6.2% Fe, 16.5% Cr, 17% Mo, and less than 1% amounts of C, V, Mn, Si, P, and S.

Yield % is the comparison of the actual weight of the reaction product with the theoretical weight of the reaction product.

Calculation: % yield=(actual weight÷theoretical weight)×100

The actual weight of the reaction product is the weight after venting of the PAF by-product of the product of the reaction, followed by washing of the remainder of the reaction product to obtain the purified reaction product. The theoretical weight of the reaction product is obtained from the following calculation: the weight of the iodine+the weight of the $CF_2$ (difluorocarbene) from the HFPO=(50/166)×wt. of HFPO).

The GC analysis results disclosed herein for the process of the present invention are taken from CG analysis on the purified reaction product after (i) removal of perfluoroacetyl fluoride (PAF) by cooling the direct reaction product to 0° C. and (ii) venting the gas from the reactor and (iii) then washing of the remaining reaction product.

The washing referred to herein is carried out using an aqueous solution that is iodine removing, whereby the washing of the remaining reaction product removes the trace amounts of unreacted iodine and any water soluble materials. The aqueous solution can be for example a saturated solution of sodium bisulfite. The washing is conveniently carried out at ambient temperature (15° C. to 25° C.), At the completion of the HFPO/iodine reaction, after removal of PAF, it can be considered that there are two reaction products, as follows: (1) the reaction product obtained directly from the reaction, i.e. the direct reaction product, and (2) the reaction product resulting from washing of the direct reaction product such as with saturated aqueous solution of sodium bisulfite at ambient temperature (15° C. to 25° C.). The reaction product (2) is herein referred to as the purified reaction product mentioned above. The weight loss from this wash is very little as compared to the weight of the direct reaction product (1). In the % yield calculation, the actual weight of the reaction product is the weight of the purified reaction product.

The temperature at which the HFPO/iodine reaction is carried out, also referred to herein as the reaction temperature and the like, and the temperature of heating to at least 220° C. to decompose the compounds $ICF_2I$ and $I(CF_2)_2I$, as disclosed herein all mean the temperature of the content of the reactor, i.e. the temperature in the interior of the reactor at the time of the event, either reaction or heating to decompose the contaminants. In the small reactors used in the Examples, the temperature of the reactor, sometimes referred to as a tube, and its content are the same, as determined by comparison of temperature readings when the thermocouple location is varied between reactor exterior surface and reactor interior. Thus, the temperatures reported in the Examples are actually the temperature of the content of the reactor. In the Examples, the cooling of the reactor is to 0° C., which is also the temperature of the content of the reactor. In large reactors, the temperature thermocouple would be placed within the interior of the reactor to provide the interior temperature, such as reaction temperature, decomposition temperature, or cooling temperature, as the case may be.

Example 1

HFPO/Iodine Molar Ratio=3.0

In a 400 mL shaker tube, was charged iodine (50.8 grams, 0.2 moles), and HFPO (hexafluoropropylene oxide) (99.6 grams, 0.60 moles) was transferred into the tube (reactor) under cool-evacuation condition. The tube was heated at 190° C. for 8 hrs, and at 230° C. for 6 hrs. The heating at 190° C. caused the HFPO to react with the iodine, and the subsequent heating at 230° C. eliminated practically all of the $ICF_2I$ and $I(CF_2)_2I$ compounds from the reaction product. The tube was cooled, vented, and this liquid reaction product was collected, and washed with saturated sodium bisulfite aqueous solution to form the purified reaction product. This reaction product weighed 68.0 grams, which amounts to 84.2 wt % yield of the theoretical weight of the reaction product that should have been obtained from the amounts of reactants used. The purified reaction product was examined by GC for the PDA distribution, as follows: PDA-3 (GC area 95.6%), PDA-1 (0.18%), PDA-2 was not detectable.

This experiment indicated that while the two-step process of first carrying out the chemical reaction, followed by heating at higher temperature, gave a high selectivity in terms of high PDA-3 formation and very low PDA-1 and PDA-2 formation, the yield of reaction product amount (wt %) was lower than desired. In Examples that follow, the presence of a greater amount (molar ratio) of HFPO results in a high selectivity of a greater yield of reaction product, and as a result thereof, a greater amount of the desired $I(CF_2)_nI$, wherein n is 3 to 7.

Table I lists the experiments (Examples) in 400 mL shaker tubes and 1,300 mL rocker tubes and these Examples follow the Table.

TABLE I

| Example | Reactor | Yield (%) | Rx. Conditions | PDA-3 (%) | PDA-1 | PDA-2 | PDA-4 | PDA-5 | PDA-6 | PDA-7 |
|---|---|---|---|---|---|---|---|---|---|---|
| 2 | 400 S | 90.5 | 190 (8), 230 (4.5) | 76.9 | 0.06 | 0.00 | 2.62 | 16.67 | 1.63 | 1.89 |
| 3 | 1,300 R | 95.3 | 190 (8), 230 (6) | 75.7 | 0.03 | 0.01 | 2.47 | 16.47 | 1.60 | 1.91 |
| 4 | 400 S | 93.0 | 190 (4), 230 (3) | 72.8 | 0.03 | 0.01 | 2.56 | 17.94 | 1.58 | 2.33 |
| 5 | 1,300 R | 94.3 | 190 (6), 230 (4.5) | 73.3 | 0.03 | 0.00 | 2.40 | 17.07 | 1.55 | 2.10 |

Rx conditions=Temperature (° C.)/[Hours at that temperature, first at 190° C. and then at 230° C.]; The product distribution was determined by GC (in area %). The HFPO/Iodine=3.5 (molar ratio) were used in these experiments. The GC area selectivity of PDA-3 to PDA-7 is at least 96% for Examples 1-5.

Example 2

The procedure of this Example is the same as for Example 4 described below, except as indicated in Table 1. The results are reported in Table I.

Example 3

In a 1,300 mL rocker tube was charged iodine (152.4 grams, 0.6 moles) and HFPO (hexafluoropropylene oxide) (348 grams, 2.1 moles) was transferred into the tube under cool-evacuation condition. The tube was heated at 190° C. for 8 hrs, and at 230° C. for 6 hrs. The tube was cooled, vented, and the liquid direct reaction product was collected and washed with saturated sodium bisulfite aqueous solution, and a pale yellowish brown purified reaction product was obtained (245.2 grams, yield of 95.3%). The purified reaction product was examined by GC for the PDA distribution. The main composition was PDA-3 (75.7 GC area %), and the PDA-1 content ($CF_2I_2$) was 0.03 GC area %, PDA-2 (I—$CF_2CF_2$—I) was 0.01%. The amount of other PDAs are reported in Table I.

Example 4

In a 400 mL shaker tube was charged iodine (50.8 grams, 0.2 moles) and HFPO (hexafluoropropylene oxide) (116 grams, 0.70 moles) was transferred into the tube under cool-evacuation condition. The tube was heated at 190° C. for 4 hrs, and at 230° C. for 3 hrs. The tube was cooled, vented, and the liquid direct reaction product was collected, and washed with saturated sodium bisulfite aqueous solution. The resultant purified reaction product (79.7 grams, yield 93.0%) was examined by GC for the PDA distribution. The main composition was PDA-3 (72.8 GC area %), and the PDA-1 ($CF_2I_2$) was 0.06 area %, while PDA-2 was not detectable, other PDA's are listed in the table. The PDA-3 is further identified by NMR analysis ($^{19}$F-NMR ($CDCl_3$, 376.89 MHz): −58.0 (m, 4F), −105.2 (m, 2F)).

Example 5

The procedure of Example 3 was repeated, except the first stage heating conditions were 190° C. for 6 hrs and the second stage heating conditions were 230° C. for 4.5 hrs. The purified reaction product weighed 242.5 g, which corresponds to a 94.3% theoretical yield. The results are reported in Table I.

Table II lists the experiments in 1-Gallon Reactor for Examples 6 to 13

| Example | Yield (%) | Rx. Conditions | PDA-3 (%) | PDA-1 | PDA-2 | PDA-4 | PDA-5 | PDA-6 | PDA-7 |
|---|---|---|---|---|---|---|---|---|---|
| 6 | 80.6 | 190 (8), 230 (6) | 89.9 | 0.41 | 0.00 | 0.71 | 0.86 | 0.15 | N/A |
| 7 | 80.7 | 190 (8), 230 (6) | 91.6 | 0.86 | 0.00 | 0.78 | 0.71 | N/A | N/A |
| 8 | 80.2 | 190 (8), 230 (6) | 94.0 | 0.56 | 0.04 | 0.81 | 0.78 | 0.14 | N/A |
| 9 | 90.2 | 190 (8), 230 (6) | 88.2 | 0.00 | 0.01 | 0.94 | 5.36 | 0.92 | 0.18 |
| 10 | 76.5 | 190 (8), 230 (6) | 90.2 | 0.62 | 0.07 | 0.76 | 0.75 | 0.17 | N/A |
| 11 | 71.3 | 190 (8), 230 (6) | 91.5 | 0.76 | 0.05 | 0.87 | 0.77 | 010 | N/A |
| 12 | 71.0 | 190 (8), 230 (6) | 95.9 | 0.90 | 0.00 | 0.93 | 0.81 | N/A | N/A |
| 13 | 74.8 | 190 (8), 230 (6) | 96.3 | 0.65 | 0.03 | 1.02 | 0.94 | N/A | N/A |

Rxconditions=Temperature (° C.)/[Hours at that temperature]; the PDA production distribution was determined by GC (in area %); the HFPO/Iodine=3.5 (molar ratio) was used in these Examples. The combined GC area selectivity of PDA-3 to PDA-7 is at least 90% for these Examples 7-13.

Example 6

In a one-gallon reactor was charged iodine (457.2 grams, 1.8 moles) and HFPO (hexafluoropropylene oxide) (1,046 grams, 6.3 moles) was transferred into the reactor under cool-evacuation condition. The reactor was heated at 190° C. for 8 hrs, and at 230° C. for 6 hrs. The reactor was cooled, vented, and the liquid reaction product was collected, and washed with saturated sodium bisulfite aqueous solution. The resultant purified reaction product (622.7 grams, 80.6%) was examined by GC for the PDA distribution. The main composition was PDA-3 (89.9 GC area %), and the PDA-1 ($CF_2I_2$) was 0.41 area %, while PDA-2 was not detectable. The analysis for additional PDAs is reported in Table II.

Example 7

Example 6 was repeated and the results are reported in Table II.

Example 8

Example 6 was repeated and the results are reported in Table II.

Example 9

In a one-gallon reactor was charged iodine (457.2 grams, 1.8 moles) and HFPO (hexafluoropropylene oxide) (1,046 grams, 6.3 moles) was transferred into the reactor under cool-evacuation condition. The reactor was heated at 190° C. for 8 hrs, and at 230° C. for 6 hrs. The reactor was cooled, vented and the liquid reaction product was collected, and washed with saturated sodium bisulfite aqueous solution. The resultant purified reaction product (696.2 grams, 90.2%) was examined by GC for the PDA distribution. The main composition was PDA-3 (88.2 GC area %), and the PDA-1 ($CF_2I_2$) was not detectable, while PDA-2 was in 0.01 area %. The analysis for other PDAs is reported in Table II.

Examples 10-13

These Examples are a repetition of Example 9 and the analysis results are reported in Table II.

Example 14 HFPO/Iodine=3.0

In a one-gallon reactor was charged iodine (457.2 grams, 1.8 moles) and HFPO (hexafluoropropylene oxide) (894 grams, 5.4 moles) was transferred into the reactor under cool-evacuation condition. According to the two-step process, the reactor was heated at 190° C. for 8 hrs, and at 230° C. for 6 hrs. The reactor was cooled, vented, and the liquid reaction product was collected, and washed with saturated sodium bisulfite aqueous solution. The resultant purified reaction product (217 grams, 29.8%) was examined by GC for the PDA distribution, PDA-3 (GC area 95.3%), PDA-1 (1.27%), PDA-2 (0.60%). This Example obtains a small yield of reaction product and excessive amounts of PDA-1 and PDA-2, reinforcing the preference for the HFPO/iodine molar ratio being at least 3.3 together with the practice of the two-step process.

Example 15

In a one-gallon reactor was charged iodine (1028.7 grams, 4.05 moles) and HFPO (hexafluoropropylene oxide) (2,354 grams, 14.2 moles) (HFPO/iodine molar ratio of 3.5) was transferred into the reactor under cool-evacuation condition. The reactor was heated at 190° C. for 8 hrs, and at 230° C. for 6 hrs under vigorous agitation. The reactor was cooled, vented, and the liquid reaction product was collected, and washed with saturated sodium bisulfite aqueous solution. The resultant purified reaction product (1481.6 grams, 85.3%) was examined by GC for the PDA distribution. The main composition was PDA-3 (89.5 GC area %), and the PDA-1 ($ICF_2I$) was 0.23 GC area %, while PDA-2 was not detectable. The results of the Example are reported in Table III.

Example 16

In a one-gallon reactor was charged iodine (1028.7 grams, 4.05 moles) and HFPO (hexafluoropropylene oxide) (2,354 grams, 14.2 moles) (HFPO/iodine molar ratio of 3.5) was transferred into the reactor under cool-evacuation condition. The reactor was heated at 190° C. for 8 hrs, and at 230° C. for 6 hrs under vigorous agitation. The reactor was cooled, vented, and the liquid reaction product was collected, and washed with saturated sodium bisulfite aqueous solution. The resultant purified reaction product (1437.8 grams, 82.7%) was examined by GC for the PDA distribution. The main composition was PDA-3 (95.4 GC area %), and the PDA-1 ($ICF_2I$) was 0.14 GC area %, while PDA-2 was not detectable. The results of the Example are reported in Table III Table III lists the experiments in 1-Gallon Reactor

| Example | Yield (%) | Rx. Conditions | PDA-3 (%) | PDA-1 | PDA-2 | PDA-4 | PDA-5 | PDA-6 | PDA-7 |
|---|---|---|---|---|---|---|---|---|---|
| 15 | 85.3 | 190 (8), 230 (6) | 89.5 | 0.23 | <0.02 | 0.79 | 0.91 | N/A | N/A |
| 16 | 82.7 | 190 (8), 230 (6) | 95.4 | 0.14 | 0.00 | 0.93 | 1.65 | 0.60 | N/A |
| 17 | 87.9 | 190 (8), 230 (6) | 92.2 | 0.33 | 0.04 | 1.03 | 1.06 | 0.33 | N/A |
| Comparison A | <70.0 | 190 (8) | 91.2 | 5.45 | 0.22 | 0.78 | 0.65 | N/A | N/A |

Example 17

Example 16 was repeated and the results are reported in Table III.

Comparison Example A

Reaction

Temperature Only at 190° C., No 230° C. Heating

In a one-gallon reactor was charged iodine (1028.7 grams, 4.05 moles) and HFPO (hexafluoropropylene oxide) (2,354 grams, 14.2 moles) (HFPO/iodine molar ratio=3.5) was transferred into the reactor under cool-evacuation condition. The reactor was heated only at 190° C. for 8 hrs. The reactor was cooled, vented, and the liquid reaction product was collected, and washed with saturated sodium bisulfite aqueous solution. The resultant purified reaction product was examined by GC for the PDA distribution, PDA-3 (GC area 91.2%), PDA-1 (5.45%), PDA-2 (0.22%). This experiment indicated that without the higher temperature (230° C.) heating, the residual PDA-2, and especially PDA-1 residual amounts were excessive. Addition of the higher temperature heating in Examples 15-17 resulted in the PDA-1 ($ICF_2I$) decreasing to 0.14 area %, while PDA-2 became not detectable. The results of this Comparison Example are reported in Table III.

Example 18

Vent-Charge Cycle

In a 400 mL shaker tube was charged iodine (50.8 grams, 0.2 moles) and the intended HFPO quantity (hexafluoropropylene oxide) (116 grams, 0.70 moles) was charged into the reaction in a 3-stage cycle. Each transfer was through a cool-evacuation process.

Stage I: First portion of HFPO (38.7 grams, 0.233 moles) was transferred into the reaction tube. The tube was heated at 190° C./4 hrs (step (a)) then at 230° C. for 1 hr. The tube was cooled to 0° C. (step (b)), and the gas phase material was released and removed, i.e. vented (step (c)) (and also passed through a scrubber with 40% KOH/aqueous solution);

Stage II: The reaction tube was further cooled to −78° C. in a dry-ice/acetone bath, then the second portion of HFPO (38.7 grams, 0.233 moles) was transferred into the reaction tube. The tube was heated at 190° C./4 hrs (step (a)), then at 230° C. for 1 hr; the tube was again cooled to 0° C. (step (b)), and the gas phase material was vented (step (c));

Stage III: The reaction tube was further cooled to −78° C. in a dry-ice/acetone bath, then the third portion of HFPO (38.7 grams, 0.233 moles) was transferred into the reaction tube. The tube was heated at 190° C./4 hrs (final step (a)), then at 230° C. for 8 hr; the final product mixture, after final steps (b) and (c), was worked up by sodium bisulfite wash as previously described. The total amount of HFPO reacted with the iodine was 3.5 mols of the HFPO/per mol of iodine. The resultant purified reaction product (73.0 grams, 85.1% yield) was examined by GC. PDA-3 has an area 72.2%, and PDA-1 and PDA-2 has an area 0.05% and 0.02 area % respectively. All the PDAs detected accounted for 97.47 area % of the entire purified reaction product.

Like results are obtained when the heating to 230° C. is carried out only on the direct reaction product resulting from the final step (a).

Example 19

Example 18 was repeated except that added catalyst was present in the shaker tube for each stage of the reaction. The catalyst added to the shaker tube was 5 g Ni ProPack® plus 10 g. Mo wire. The result of this experiment was a purified reaction product giving the following GC analysis: PDA-1=0.17 area %, PDA-2=0.00 area %, PDA-3=81.30 area %, PDA-4=1.50 area %, PDA-5=12.50 area %, PDA-6=1.15 area %, and PDA-7=0.97 area %, totaling 97.59 area %. The benefit of the added catalyst is primarily reducing the small amount of PDA-2 from 0.02 area % of Example 18 to non-detectible.

What is claimed is:

1. A process comprising forming a stable mixture comprising $I(CF_2)_nI$, wherein n is at least 3 and at least one of $I(CF_2)_nI$, wherein n is 1 or 2, as a contaminant in said mixture and heating said mixture to a temperature of at least 220° C. to reduce the amount of said contaminant to be no greater than 1% when said contaminant is $ICF_2I$ and no greater than 0.1% when said contaminant is $ICF_2CF_2I$.

2. The process of claim 1 wherein said stable mixture is the reaction product of a chemical reaction in a reactor.

3. The process of claim 2 wherein said chemical reaction is without the need for catalyst being present.

4. The process of claim 1 wherein said stable mixture contains $I(CF_2)_3I$ as the predominant component.

5. The process of claim 4 wherein said chemical reaction is between iodine and hexafluoropropylene oxide.

6. The process of claim 5 wherein said $I(CF_2)_nI$, wherein n is at least 3 is the homologue mixture of $I(CF_2)_nI$ wherein n is 3 to 7 and said $I(CF_2)_nI$, wherein n is 3, comprises at least 70% of said homologue mixture.

7. The process of claim 6 wherein the yield of said homologue mixture is at least 70%.

8. The process of claim 7 wherein said chemical reaction between said iodine and said hexafluoropropylene oxide is carried out at a temperature of 150° C. to 210° C. prior to heating said mixture to a temperature of at least 220° C.

9. The process of claim 8 wherein the molar proportion of said hexafluoropropylene oxide to said iodine in said chemical reaction is at least 3.0.

10. The process of claim 8 wherein the molar proportion of said hexafluoropropylene oxide to said iodine in said chemical reaction is at least 3.3.

* * * * *